United States Patent
Brafford et al.

(10) Patent No.: US 7,270,790 B2
(45) Date of Patent: Sep. 18, 2007

(54) STERILIZER MONITORING AND CONTROLLING SYSTEM AND METHOD

(75) Inventors: Bob Brafford, Grayslake, IL (US); Alex Kapustyan, Grayslake, IL (US)

(73) Assignee: Baxter International Inc., Deerfield, IL (US)

( * ) Notice: Subject to any disclaimer, the term of this patent is extended or adjusted under 35 U.S.C. 154(b) by 695 days.

(21) Appl. No.: 10/120,852

(22) Filed: Apr. 11, 2002

(65) Prior Publication Data

US 2003/0194344 A1    Oct. 16, 2003

(51) Int. Cl.
*H05B 41/36* (2006.01)

(52) U.S. Cl. .................. 422/105; 315/291; 315/299; 315/307

(58) Field of Classification Search .......... 422/3, 422/105; 315/291, 299, 307; 324/76.12; 250/455.11
See application file for complete search history.

(56) References Cited

U.S. PATENT DOCUMENTS

| | | | | |
|---|---|---|---|---|
| 3,320,477 A | * | 5/1967 | Boeker | 315/307 |
| 3,544,913 A | * | 12/1970 | Anderson | 327/538 |
| 3,921,070 A | * | 11/1975 | Ringstad et al. | 324/142 |
| 4,400,270 A | | 8/1983 | Hillman | |
| 4,652,763 A | | 3/1987 | Nablo | 250/292.3 |
| 4,788,126 A | | 11/1988 | Feldman et al. | 430/138 |
| 4,788,494 A | * | 11/1988 | Faulkner | 324/142 |
| 4,819,125 A | * | 4/1989 | Arinobu et al. | 361/97 |
| 5,084,623 A | | 1/1992 | Lewis et al. | 250/474.1 |
| 5,099,132 A | | 3/1992 | Ueno et al. | 250/474.1 |
| 5,310,987 A | * | 5/1994 | Rutz | 219/121.34 |
| 5,446,289 A | * | 8/1995 | Shodeen et al. | 250/455.11 |
| 5,451,794 A | | 9/1995 | McKeown et al. | 250/492.3 |
| 5,557,109 A | | 9/1996 | Bidnyy et al. | 250/455.11 |
| 5,574,654 A | * | 11/1996 | Bingham et al. | 702/62 |
| 5,801,387 A | | 9/1998 | Nablo et al. | 250/492.3 |
| 5,869,833 A | | 2/1999 | Richardson et al. | 250/310 |
| 6,030,554 A | | 2/2000 | Ichihara | 252/583 |
| 6,140,657 A | | 10/2000 | Wakalopulos et al. | 250/492.3 |

(Continued)

FOREIGN PATENT DOCUMENTS

JP      07020296 A  *  1/1995

(Continued)

OTHER PUBLICATIONS

Machine Translation for JP 07020296A, http://www19.ipdl.ncipi.go.jp/PA1/cgi-bin/PA1INIT?1112640183462.*

(Continued)

Primary Examiner—Gladys J P Corcoran
Assistant Examiner—Sean E. Conley
(74) Attorney, Agent, or Firm—Austin J. Foley; Bell, Boyd & Lloyd LLC

(57) ABSTRACT

A system and method are provided for monitoring and/or controlling a sterilization system. Briefly described, in architecture, the system can be implemented as follows. A current transformer is operatively associated with a source of power for a radiation source. A power meter is operatively associated with the source of power. The power meter is also operatively associated with the current transformer. The power meter is designed to monitor the source of power to confirm the radiation source provides a desired dosage.

25 Claims, 7 Drawing Sheets

U.S. PATENT DOCUMENTS

| | | | |
|---|---|---|---|
| 6,191,424 B1 | 2/2001 | Stirling et al. | 250/455.11 |
| 6,320,935 B1 | 11/2001 | Shinar et al. | 378/119 |
| 6,617,596 B1 * | 9/2003 | Korenev | 250/492.3 |
| 6,624,600 B1 * | 9/2003 | Henze | 315/291 |
| 2002/0175299 A1 * | 11/2002 | Kanie et al. | 250/504 R |

FOREIGN PATENT DOCUMENTS

| | | |
|---|---|---|
| WO | WO 01/19687 | 3/2001 |
| WO | WO 01/19687 A1 * | 3/2001 |
| WO | WO 03/086482 | 10/2003 |

OTHER PUBLICATIONS

A-B Quality, Bulletin 1404 Powermonitor 3000 Master Module and Display Module, pp. i-iv, P1-P2, and 1-1-1-5, Publication 1404-IN001A-US-P.

I-AX Technologies, "Online Sterilization: A Different Approach to Sterilization for High Value Single Use Medical Devices," http://www.iaxtech.com/online_sterilization.htm, pp. 1-2.

National Physical Laboratory, "Mail-Order Reference Dosimetry Service for Radiation Processing," http://www.npl.co.uk/npl/rad/services/mail.html, pp. 1-2.

Zavadtsev, A.A., "Electron Beam Scanning System." 1998, pp. 3860-3862.

Snyder, O.P. & Poland, D.M., "Food Irradiation Today," http://www.hi-tm.com/Documents/Irrad.html, 1995, pp. 1-20, Hospitality Institute of Technology and Management.

Travish, J., Biedron, S., Borland, M., Hahne, M., Harkay, K., Lewellen, J., Lumpkin, A., Milton, S. Sereno, N., "High-Brightness Beams from a Light Source Injector: The Advanced Photon Source Low-Energy Undulator Test Line LINAC," http://www.slac.stanford.edu/edonf/C000821/THC19.shtml, pp. 1-3.

Jennings, W.A., "The History of Radiation Dosimety," http://www.npl.co.uk/npl/rad/features/history/d1.gif, p. 1, National Physical Laboratory.

Jennings, W.A., "The History of Radiation Dosimety," http://www.npl.co.uk/npl/rad/features/history/d2.gif, p. 1, National Physical Laboratory.

Jennings, W.A., "The History of Radiation Dosimety," http://www.npl.co.uk/npl/rad/features/history/d3.gif, p. 1, National Physical Laboratory.

Report from Sargent & Krahn regarding Chilean Patent Application No. 752-2003 in the Name of Baxter International Inc. dated Mar. 7, 2007.

* cited by examiner

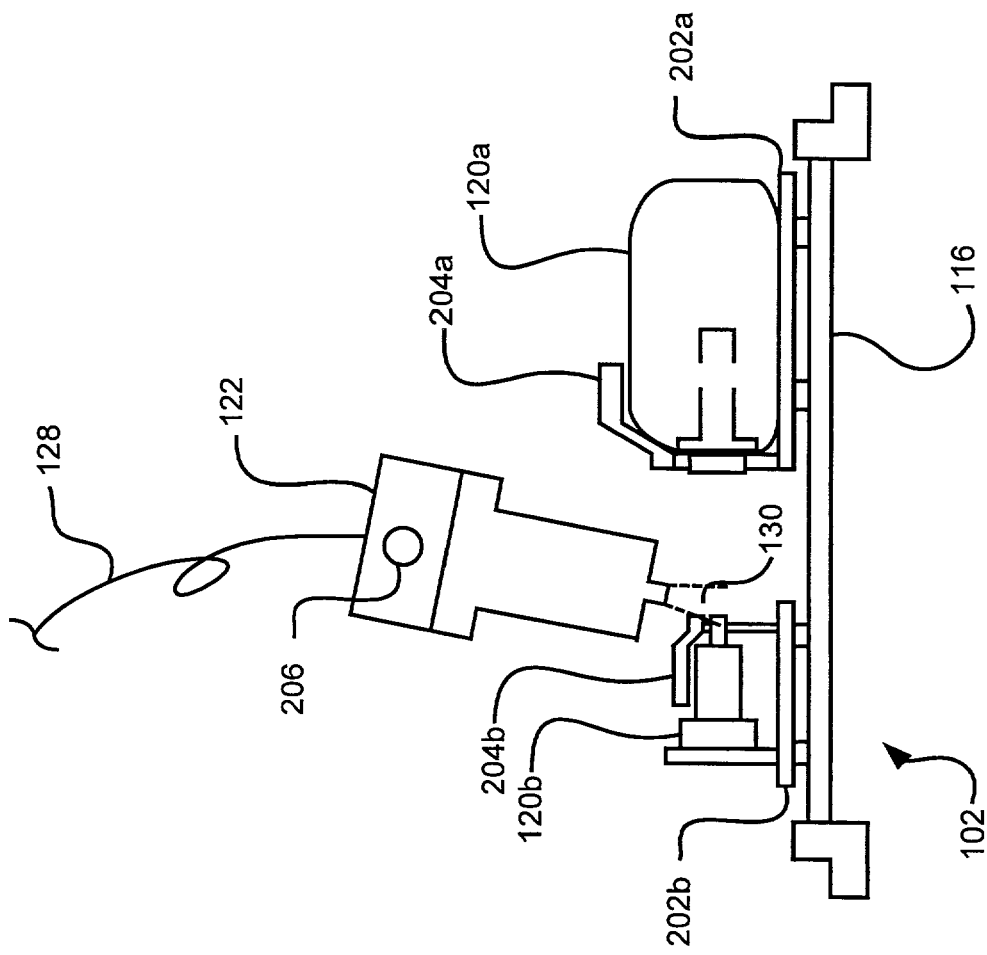

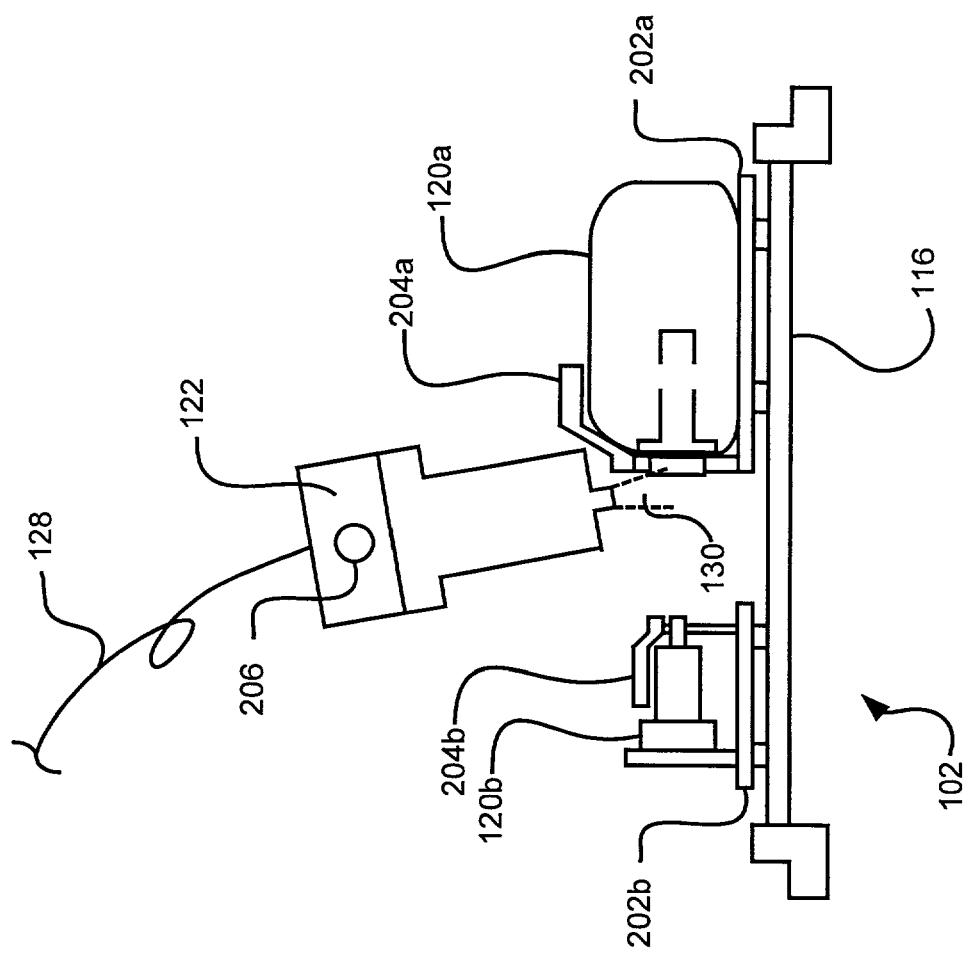

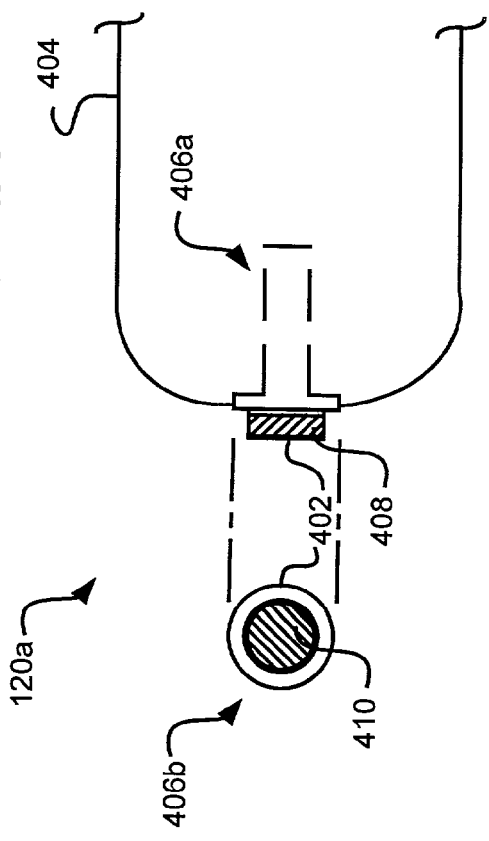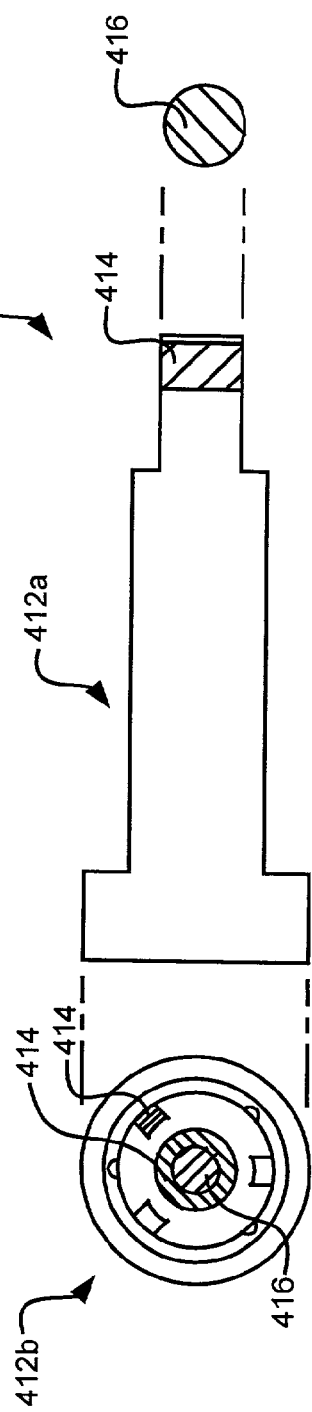

STERILIZER MONITORING AND CONTROLLING SYSTEM AND METHOD

TECHNICAL FIELD

The present invention is generally related to systems for sterilizing medical packaging components and, more particularly, is related to a system and method for monitoring and/or controlling the sterilization system.

BACKGROUND

Large doses of radiation will kill microorganisms. In recent years the medical industry has introduced radiation to sterilize medical products that do not lend themselves to traditional sterilization systems such as those based on heat and steam. Particular interest has focused on sterilization of plastic disposables such as syringes and blood transfusion sets, as well as complex apparatus such as heart-lung machines and kidney dialysis units.

Electron beam irradiation sterilization is one type of radiation-based sterilization system. The quality of sterilization is determined by the dose of radiation applied to the kill zone. The dose is determined by factors such as beam current, electron energy, and beam scanning system parameters. The dose in the kill zone may be estimated by securing dosage meters to areas near the kill zone and correlating the dosage reading with known actual kill rates for the read dosage readings. Alternatively, dosage meters may be applied to the kill zone in preliminary production runs. However, sterilization methods that rely upon reading dosage meters applied to the packaging components throughout the production run are inconvenient and expensive.

SUMMARY

The present invention provides a system and method for monitoring and/or controlling a sterilization system. Briefly described, in architecture, the system can be implemented as follows. A current transformer is operatively associated with a source of power for a radiation source. A power meter is operatively associated with the source of power. The power meter is also operatively associated with the current transformer. The power meter is designed to monitor the source of power to confirm the radiation source provides a desired dosage.

The present invention can also be viewed as providing a method for monitoring and/or controlling a sterilization system. In this regard, the method can be broadly summarized by the following steps: (1) determining the current provided to a radiation source by a power source; (2) determining the voltage of the power source; and (3) monitoring the current and the voltage to confirm a desired kill rate is provided by the radiation source.

The invention may also be viewed as a computer program for controlling a sterilizer. The program includes: (1) logic for determining a kill zone; (2) logic for determining kill rates in the kill zones for a plurality of sterilizing radiation source input powers; (3) logic for determining a desired kill rate; (4) logic for determining the input power required to achieve the desired kill rate; (5) logic for setting the input power; and (6) logic for monitoring the input power to confirm the desired kill rate.

Other systems, methods, features, and advantages of the present invention will be, or will become, apparent to those having skill in the art upon examination of the following drawings and detailed description. It is intended that all such additional systems, methods, features, and advantages are included within this description, are within the scope of the present invention, and are protected by the following claims.

BRIEF DESCRIPTION OF THE DRAWINGS

The invention can be better understood with reference to the following drawings. The components in the drawings are not necessarily to scale, emphasis instead being placed upon illustrating the principles of the present invention. Moreover, in the drawings, like reference numerals designate corresponding parts throughout the several views.

FIG. 1 shows a front view of the conveyor system and a front view of the irradiation system.

FIG. 2 is a first side view of the conveyor and irradiation systems of FIG. 1.

FIG. 3 is a second side view of the conveyor and irradiation systems of FIG. 1.

FIGS. 4A and 4B are enlarged views of the medication packaging components of FIG. 1. FIG. 4A shows the medication solution container including a port assembly. FIG. 4B shows the sleeve assembly.

DETAILED DESCRIPTION

Figure 1:
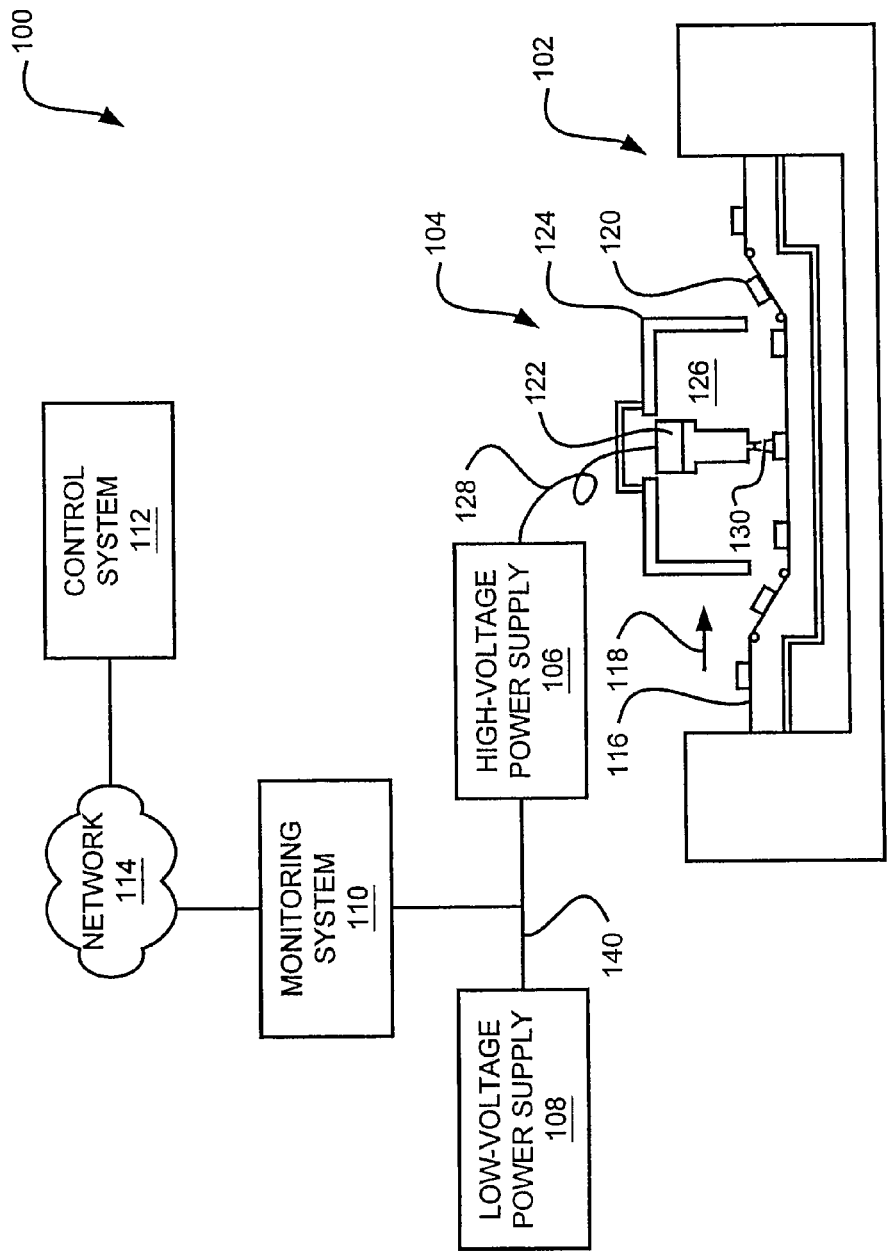
FIG. 1 is a graphical representation of a sterilization system. The sterilization system includes a conveyor system, an irradiation system, and a control system. The conveyor system is designed to transport medication packaging components. The medication packaging components include a sleeve assembly and a medication solution container.

FIG. 1 is a graphical representation of a sterilization system 100. Sterilization system 100 includes a conveyor system 102, an irradiation system 104, and a control system 112. The conveyor system 102 is designed to transport medication packaging components 120. The medication packaging components 120 include a medication solution container 120a and a sleeve assembly 120b. FIG. 1 shows a front view of the conveyor system 102 and a front view of the irradiation system 104. Sterilization system 100 also includes a high-voltage power supply 106, a low-voltage power supply 108, and a power monitoring system 110. The power monitoring system 110 and the control system 112 may communicate via a network 114.

Conveyor system 100 includes a track 116 moving in the direction indicated by arrow 118. Track 116 conveys medication packaging components 120. Irradiation system 114 includes radiation source 122. Radiation source 122 is enclosed in primary shield 124. Primary shield 124 defines cavity 126. The medication packaging components 120 are transported on track 116 through cavity 126 where the components 120 are exposed to sterilizing radiation 130 produced by radiation source 122.

Radiation source 122 is powered by high-voltage power supply 106 and is connected to power supply 106 by lead 128. High-voltage power supply is powered by low-voltage power supply 108 via lines 140 (shown as a single line in FIG. 1 and as multiple lines in FIG. 5). Lines 140 are monitored by power monitoring system 110. Control system 112 may be used to control the sterilization system 100. Tn particular, control system 112 may be used to control the dosage of sterilizing radiation 130 applied to the medication packaging components 120. The control system 112 may control the dosage using data provided by power monitoring system 110. In other embodiments, the sterilization system 100 may be designed to deliver a determined dose of radiation 130 and the system 100 is monitored to confirm the determined dose is delivered to the medication packaging components 120.

FIG. 2 is a first side view of the conveyor and irradiation systems 102 and 104 of FIG. 1. In FIG. 2, track 116 may be viewed as moving toward the viewer when in motion as indicated by arrow 118 (FIG. 1). Two portions of the medication packaging components 120, the medication solution container 120a and the sleeve assembly 120b, are shown in FIG. 2. Radiation source 122 includes a pivot 206. Pivot 206 allows radiation source 122 to move between a plurality of positions including a first position shown in FIG. 2, and a second position shown in FIG. 3.

Medication solution container 120a may be supported on track 116 by first tray 202a. Sleeve assembly 120b may be supported on track 116 by second tray 202b. Portions of medication solution container 120a that are not meant to be exposed to direct radiation 130 may be protected by first shield 204a. Similarly, portions of sleeve assembly 120b that are not meant to be exposed to direct radiation 130 may be protected by second shield 204b.

FIG. 3 is a second side view of the conveyor 102 and irradiation systems 104 of FIG. 1. FIG. 3 shows radiation source 122 in a second position where radiation 130 is being directed at portions of medication solution container 120a.

FIGS. 4A and 4B are enlarged views of the medication packaging components 120 of FIG. 1. FIG. 4A shows medication solution container 120a includes a port assembly 402 and a membrane 404. Port assembly 402 is shown in a side view 406a and a front view 406b in FIG. 4A. Portions of the port assembly 402 that are inside the membrane 404 are shown as dashed lines in FIG. 4A. First shaded areas 408 are portions of the port assembly 402 upon which dosage meters may be placed to determine the level of radiation being received at the shaded area 408 of the port assembly 402. Dosage meters that may be applied to components that are being sterilized by radiation are known to those having ordinary skill in the art. The second shaded portions 410 of the port assembly 402 are the portions of the port assembly 402 that are desired to be sterilized prior to completing the assembly of a medication packaging system. The medication packaging system (not shown) is the assembled medical packaging components 120.

FIG. 4B shows sleeve assembly 120b in a side view 412a and a front view 412b. Third shaded areas 414 show portions of the sleeve assembly 120a upon which dosage meters may be placed to determine the level of radiation being received at the third shaded areas 414 of the sleeve assembly 120b. The fourth shaded portions 416 of the sleeve assembly 120b are the portions of the sleeve assembly 120b that are desired to be sterilized prior to completing the assembly of a medication packaging system.

Figure 5:
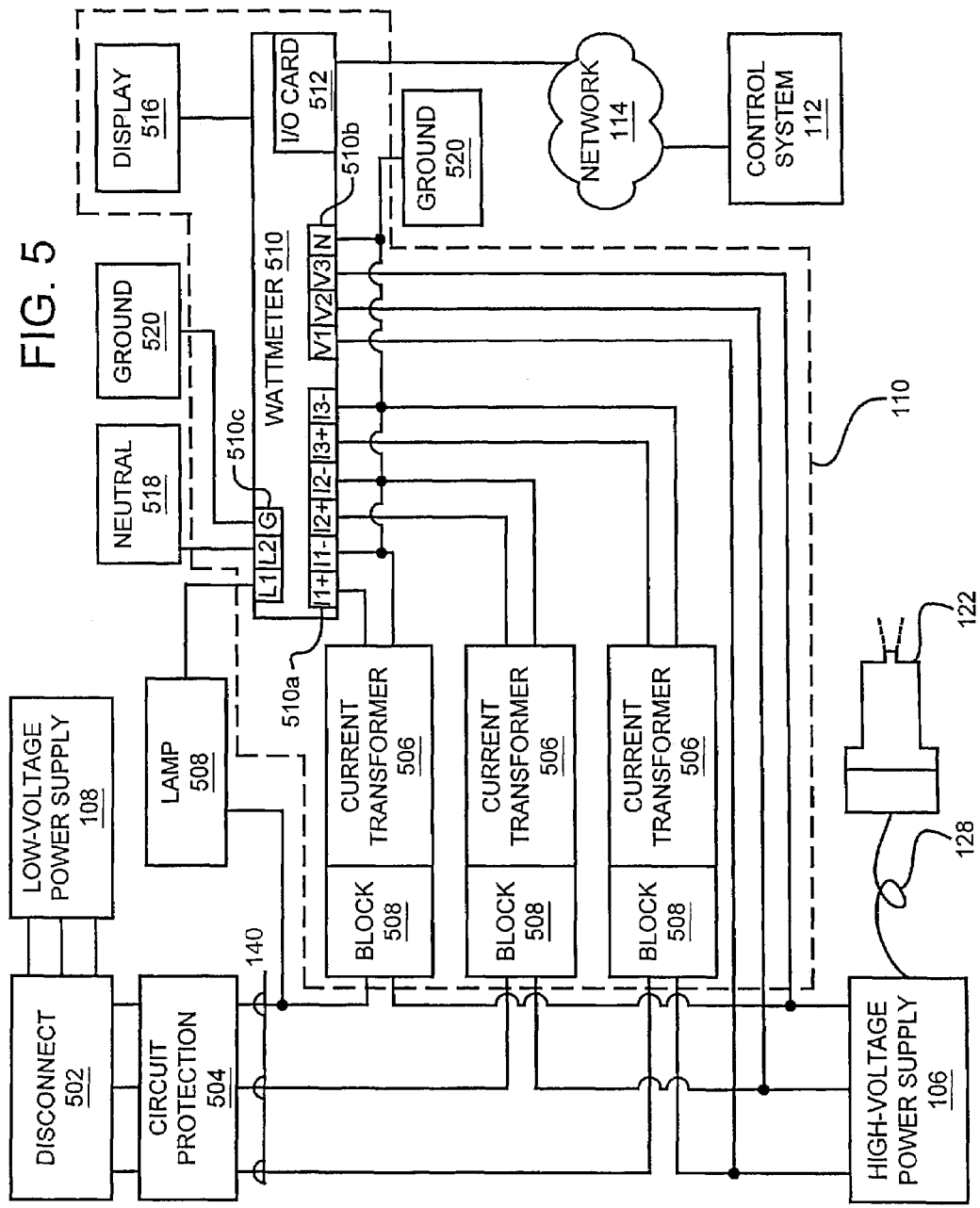
FIG. 5 shows a connection diagram for some components of the sterilization system of FIG. 1.

FIG. 5 shows a connection diagram for some components of the sterilization system 100 of FIG. 1. FIG. 5 shows the control system 112, network 114, monitoring system 110, low-voltage and high-voltage powers supplies 108 and 106, lead 128, and radiation source 122. In addition, FIG. 5 shows a disconnect 502 and a circuit protection 504 that are usually provided between low-voltage and high-voltage power supplies 108 and 106. Low-voltage power supply 108 may provide a 3-phase 208 V power supply. High-voltage power supply 106 may provide a 125 kV power supply.

Monitoring system 110 includes current transformers 506, shorting blocks 508, and wattmeter 510. Wattmeter 510 includes current connection ports 510a, voltage connection ports 510b, and control connection ports 510c. Wattmeter 510 may be provided with input output (I/O) card 512 for communicating through network 114 with control system 112. Wattmeter 510 may also be associated with lamp 514 and display 516. Wattmeter 510 is typically connected to various electrical reference points such as neutral 518 and ground 520.

Current transformers 506 may be any current transformers known in the art, such as, but not limited to, CR Magnetics current transformers having part number CR % A-SFT-201 and having a 200:5 current transformer ratio. Shorting blocks 508 may be any shorting blocks known in the art, such as, but not limited to CR Magnetics part number IKU6S. Wattmeter 510 may be any wattmeter known in the art, such as, but not limited to an Allen Bradley PowerMonitor 3000 having part number 1404-M4-05A-ENT. I/O card 512 may be any input/output card that is compatible with network 114 and wattmeter 510, such as, but not limited to an Ethernet I/O card that may be provided integrally with wattmeter 510. Display 516 may be any display compatible with wattmeter 510, such as, but not limited to Allen Bradley's display module having part number 1404-DM.

If current transformers, such as current transformers 506, are operated open circuited, extremely high voltages can be generated with resultant damage to equipment and personnel. Consequently, before removing a load such as wattmeter 510a, the current transformer should be short circuited. One method of short circuiting the current transformers 506 is through the use of a shorting blocks 508 which automatically short circuits the transformers 506 when the load is removed.

Figure 6:
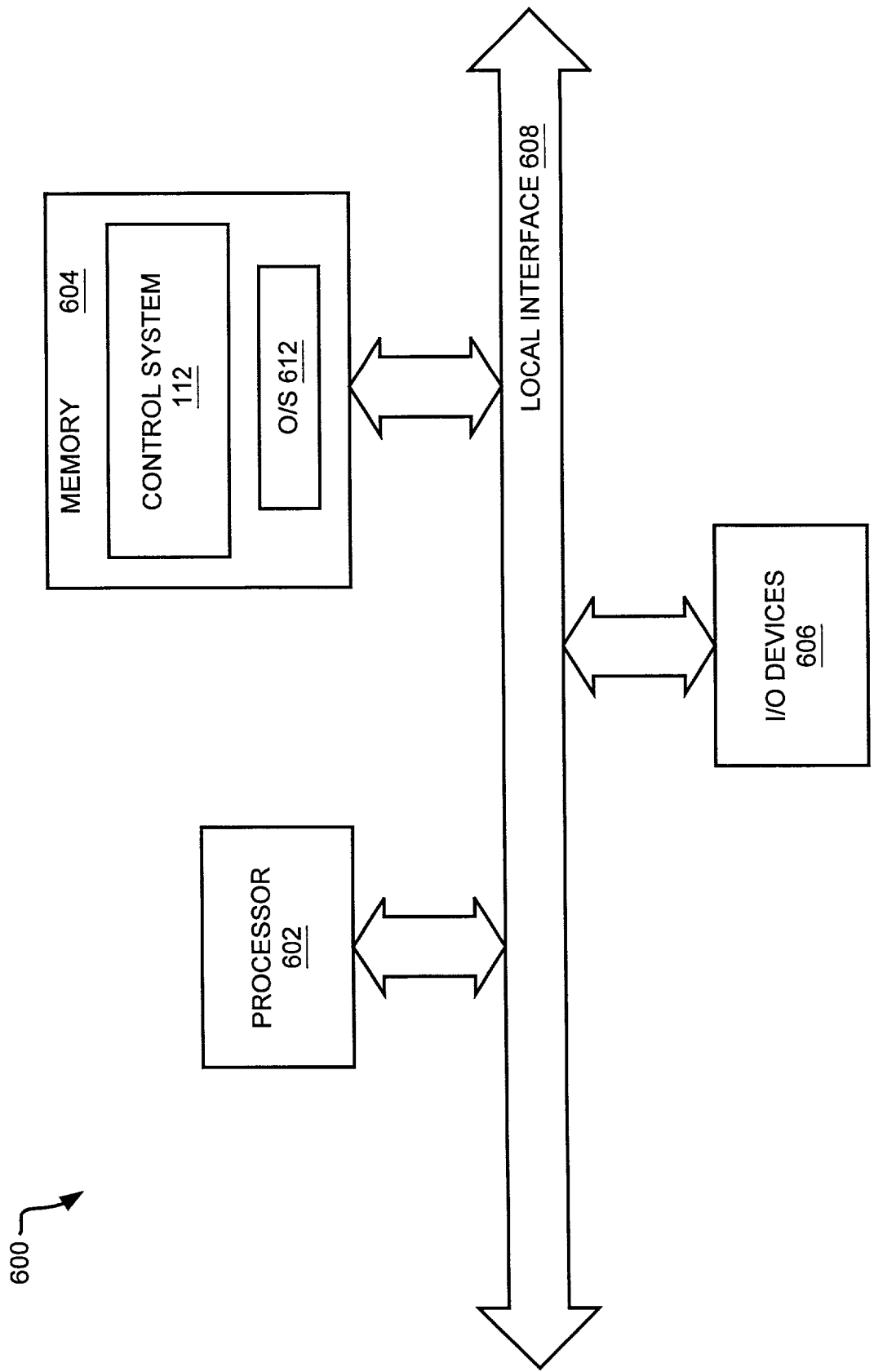
FIG. 6 shows an embodiment of the control system of FIG. 1.

In one embodiment, control system 112 is incorporated into a computer. FIG. 6 is a block diagram of a computer 600 incorporating control system 112. The control system 112 of the invention can be implemented in software (e.g., firmware), hardware, or a combination thereof. In the currently contemplated best mode, the control system 112 is implemented in software, as an executable program, and is executed by one or more special or general purpose digital computer(s), such as a personal computer (PC; IBM-compatible, Apple-compatible, or otherwise), personal digital assistant, workstation, minicomputer, or mainframe computer. An example of a general purpose computer that can implement the control system 112 of the present invention is shown in FIG. 6. The control system 112 may reside in, or have portions residing in, any computer such as, but not limited to, a general purpose personal computer. Therefore, computer 600 of FIG. 6 may be representative of any computer in which the control system 112 resides or partially resides.

Generally, in terms of hardware architecture, as shown in FIG. 6, the computer 600 includes a processor 602, memory 604, and one or more input and/or output (I/O) devices 606 (or peripherals) that are communicatively coupled via a local interface 608. The local interface 608 can be, for example, but not limited to, one or more buses or other wired or wireless connections, as is known in the art. The local interface 608 may have additional elements, which are omitted for simplicity, such as controllers, buffers (caches), drivers, repeaters, and receivers, to enable communications. Further, the local interface 608 may include address, control, and/or data connections to enable appropriate communications among the other computer components.

The processor 602 is a hardware device for executing software, particularly software stored in memory 604. Processor 602 can be any custom-made or commercially available processor, a central processing unit (CPU), an auxiliary processor among several processors associated with the computer 600, a semiconductor-based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation.

Memory 604 can include any one or a combination of volatile memory elements (e.g., random access memory (RAM, such as DRAM, SRAM, SDRAM, etc.)) and non-volatile memory elements (e.g., ROM, hard drive, tape, CDROM, etc.). Moreover, memory 604 may incorporate electronic, magnetic, optical, and/or other types of storage media. Memory 604 can have a distributed architecture where various components are situated remote from one another, but can be accessed by the processor 602.

The software memory 604 may include one or more separate programs, each of which comprises an ordered listing of executable instructions for implementing logical functions. In the example of FIG. 6, the software in the memory 604 includes the control system 112 in accordance with the present invention and a suitable operating system (O/S) 612. A non-exhaustive list of examples of suitable commercially available operating systems 612 is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal digital assistants (PDAs) (e.g.,PalmOS available from Palm Computing, Inc., and Windows CE available from Microsoft Corporation). The operating system 612 essentially controls the execution of other computer programs, such as the control system 112, and provides scheduling, input-output control, file and data management, memory management, and communication control and related services.

The control system 112 may be a source program, executable program (object code), script, or any other entity comprising a set of instructions to be performed. When the control system is a source program, the program may be translated via a compiler, assembler, interpreter, or the like, which may or may not be included within the memory 604, so as to operate properly in connection with the O/S 612. Furthermore, the control system 112 can be written as (a) an object oriented programming language, which has classes of data and methods, or (b) a procedure programming language, which has routines, subroutines, and/or functions, for example, but not limited to C, C++, Pascal, Basic, Fortran, Cobol, Perl, Java, and Ada. In one embodiment, the control system 112 is written in C++.

I/O devices 606 may include input devices, for example, but not limited to a keyboard, mouse, scanner, microphone, and touch screens. Furthermore, I/O devices 606 may also include output devices, for example, but not limited to a printer, bar code printers, displays, etc. Finally, the I/O devices 606 may further include devices that communicate both inputs and outputs, for instance, but not limited to a modulator/demodulator (modem; for accessing another device, system, or network), transceivers, a telephonic interface, a bridge, a router, etc.

If the computer 600 is a PC, workstation, PDA, or the like, the software in the memory 604 may further include a basic input output system (BIOS) (not shown in FIG. 6). The BIOS is a set of essential software routines that initialize and test hardware at startup, start the O/S 612, and support the transfer of data among the hardware devices. The BIOS is stored in ROM so that the BIOS can be executed when the computer 600 is activated.

When the computer 600 is in operation, the processor 602 is configured to execute software stored within the memory 604, to communicate data to and from the memory 604, and to generally control operations of the computer 600 pursuant to the software. The control system 112 and the O/S 612, in whole or in part, but typically the latter, are read by the processor 602, perhaps buffered within the processor 602, and then executed.

When the control system 112 is implemented in software, as is shown in FIG. 6, the control system 112 can be stored on any computer-readable medium for use by or in connection with any computer-related system or method. In the context of this document, a computer-readable medium is any electronic, magnetic, optical, or other physical device or means that can contain or store a computer program for use by or in connection with a computer-related system or method. The control system 112 can be embodied in a computer-readable medium for use by or in connection with an instruction execution system, apparatus, or device, such as a computer-based system, processor-containing system, or other system that can fetch the instructions from the instruction execution system, apparatus, or device and execute the instructions. The computer-readable medium can be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, where the control system 112 is implemented in hardware, the control system 112 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 7:
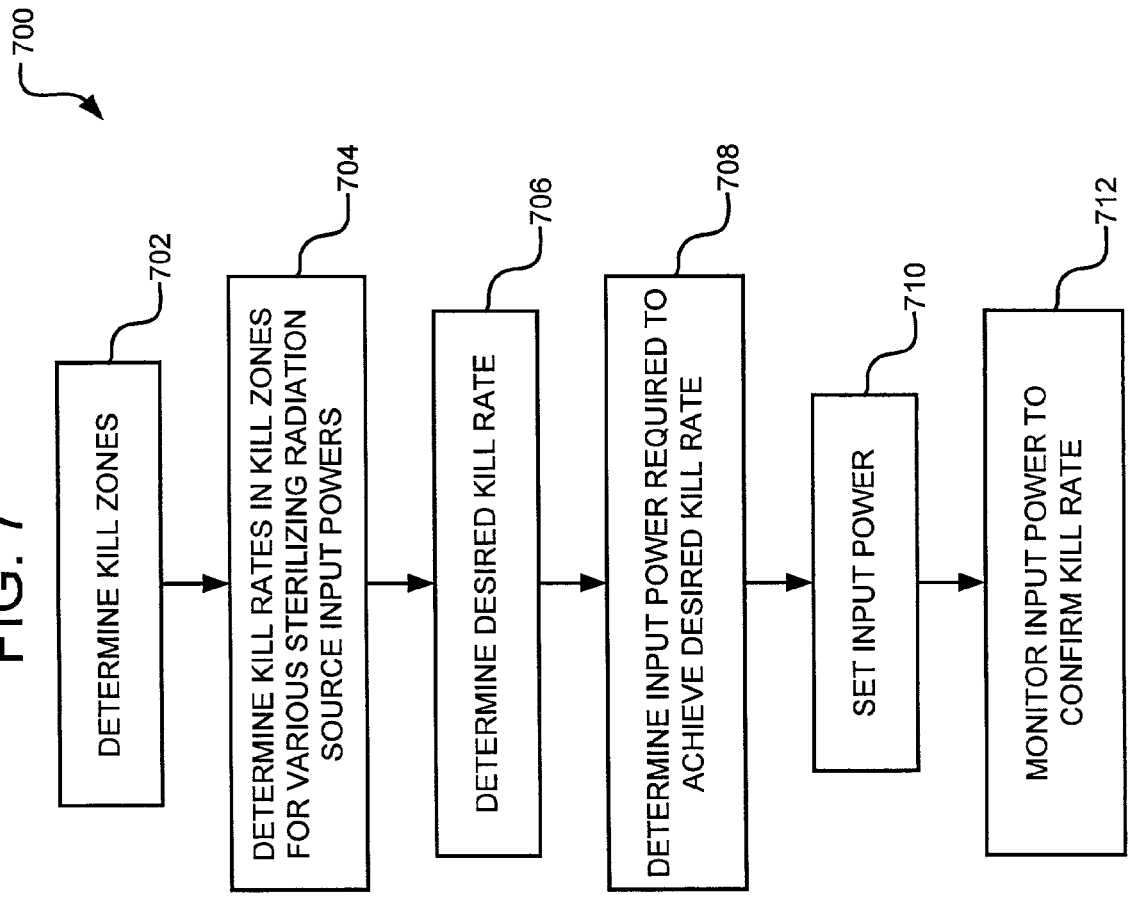
FIG. 7 shows a flowchart for the control system of FIG. 1.

FIG. 7 is a flowchart showing an exemplar embodiment 700 of control system 112. Process descriptions or blocks in figures, such as FIG. 7, should be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

In block 702 of exemplar embodiment 700, the control system 112 determines the kill zones. The kill zones are the portions of the medication packaging components 120 that must be sterile prior to the assembly of the package system. The kill zones may be, for example, but not limited to, second and fourth shaded areas 410 and 416. The kill zones may have assurance percentages associated with them. The assurance percentages provide a degree of certainty that harmful microbes within any defined area will be killed. Data from which the control system 112 determines the kill zones may be provided to the system 112 via computer I/O devices 606.

In block 704, exemplar embodiment 700 determines kill rates in the kill zones for various sterilizing radiation source 122 input powers. Data from which the control system 112 determines the kill rates may be provided to the system 112 via computer I/O devices 606. For example, dosage meters located at second and fourth shaded areas 410 and 416 may determine the dose of sterilizing radiation 130 applied to the kill zones in preliminary runs. The dose applied to the kill zones may be correlated to the kill rates, as is known to those having ordinary skill in the art. The power necessary to apply the dose may then be correlated to the kill rates. In other embodiments, the dose applied to first and third shaded areas 408 and 414 may be determined by affixing dosage meters to areas 408 and 414. After the medication packaging components 120 are passed through the sterilization system 100, the actual kill rates may be determined for the second and fourth shaded areas 410 and 416. Dosage meter readings may then be correlated to input powers and actual kill rates.

In block 706, exemplar embodiment 700 determines the desired kill rate. Data from which the control system 112 determines the desired kill rate may be provided to the system 112 via computer I/O devices 606. The data entered may simply be the kill rate. However, the data may also be more abstract information such as tables or expert systems for correlating sterilization standards, such as those published by government organizations, with the required kill rate to meet the standards.

In block 708, exemplar embodiment 700 determines the input power required to achieve the desired kill rate. The input power may be determined by referring to the data developed in block 702. In block 710, the exemplar embodiment 700 sets the input power to achieve the desired kill rate. The input power may be controlled in various manners known to those having ordinary skill in the art. In block 712, exemplar embodiment 700 monitors the input power to confirm the kill rate in the kill zone.

It is emphasized that the described embodiments of the present invention, including any preferred embodiments, are merely possible examples of implementations, merely set forth for a clear understanding of the principles of the invention. Many variations and modifications may be made to the described embodiments of the invention without departing substantially from the spirit and principles of the invention. All such modifications and variations are intended to be included within the scope of this disclosure and the present invention, and protected by the following claims.

At least the following is claimed:

1. A system for monitoring a sterilizer, the system comprising:
    a first power source;
    a current transformer, the current transformer electrically connected to the first power source;
    an electron beam radiation source having a second power source and a power output, the second power source electrically connected to the first power source and the current transformer; and
    a power meter, the power meter electrically connected to the first power source and the second power source, where the power meter is designed to monitor the first power source and the second power source to indirectly confirm that the power output of the electron beam radiation source provides a desired dosage.

2. The system for monitoring a sterilizer of claim 1, where the current transformer encircles an electrical line between the first power source and the radiation source.

3. The system for monitoring a sterilizer of claim 1, where the first power source is a 3-phase power source of less than 500 volts.

4. The system for monitoring a sterilizer of claim 1, where the power meter is designed to provide an alarm signal if the second power source is not providing a desired power to the radiation source.

5. The system for monitoring a sterilizer of claim 1, where the desired dosage is a sufficient dosage to kill harmful microbes on portions of packaging components.

6. The system for monitoring a sterilizer of claim 1, where the power meter includes an input/output card, where the input/output card is designed to communicate with a network.

7. The system for monitoring a sterilizer of claim 1, further comprising a second and a third current transformer, wherein the first power source is a 3-phase source of power and the first transformer encircles the first phase, the second transformer encircles the second phase, and the third transformer encircles the third phase.

8. The system for monitoring a sterilizer of claim 1, wherein the first power source is a low voltage power source and the second power source is a high voltage power source, where the second power source is designed to provide a sufficient voltage to power the radiation source.

9. The system for monitoring a sterilizer of claim 1, further comprising a control system, where the control system is designed to set the output of the second power source based on a desired dosage.

10. The system for monitoring a sterilizer of claim 1, further comprising a control system, where the control system is designed to monitor the power sources to confirm a desired kill rate.

11. The system for monitoring a sterilizer of claim 1, where the power meter is operatively associated with the current transformer.

12. A system for monitoring a sterilizer, the system comprising:
    a first power source;
    an electron beam radiation source electrically connected to the first power source and having a power input from a second power source connected to the first power source;
    means for determining the current provided to the electron beam radiation source by the first power source;

means for determining the voltage of the first power source; and means for monitoring the current and the voltage of the power input from the second power source to indirectly confirm a desired kill rate is provided by the electron beam radiation source.

13. The system for monitoring a sterilizer of claim 12, where the means for determining the current provided to a radiation source by a power source includes encircling an electrical line between the first power source and the radiation source with a current transformer.

14. The system for monitoring a sterilizer of claim 12, where the source of power is a three-phase power source of less than 500 volts.

15. The system for monitoring a sterilizer of claim 12, where means for monitoring the current and the voltage to confirm a desired kill rate includes designing a power meter to provide an alarm signal if the first power source is not providing a desired power to the radiation source.

16. The system for monitoring a sterilizer of claim 12, where the desired kill rate is a radiation dosage sufficient to kill harmful microbes on portions of packaging components.

17. The system for monitoring a sterilizer of claim 12, where the means for monitoring the current and the voltage to confirm a desired kill rate includes the use of an input/output card, where the input/output card is designed to communicate with a network.

18. The system for monitoring a sterilizer of claim 12, where the means for determining the current provided to a radiation source by the first power source includes the use of first, second and third current transformers, wherein the first power source is a 3-phase power source and the first transformer encircles the first phase, the second transformer encircles the second phase, and the third transformer encircles the third phase.

19. The system for monitoring a sterilizer of claim 12, where the first power source provides power to the second power source, where the first power source is a low-voltage power source and the second power source is a high-voltage power input to the electron beam radiation source, where the second power source is designed to provide a sufficient voltage to power the radiation source.

20. The system for monitoring a sterilizer of claim 12, further comprising means for setting the output of the first power source based on a desired dosage.

21. The system for monitoring a sterilizer of claim 12, where the means for monitoring the current and the voltage to confirm a desired kill rate includes a control system.

22. A system for monitoring a sterilizer, comprising:
a low voltage power source;
a high voltage power source electrically connected to the low voltage power source;
an electron beam radiation source connected to the high voltage power source; and
a power meter connected to the low voltage power source and the high voltage power source, and receiving signals from the low voltage power source and the high voltage power source indicative of a current and a voltage from the low voltage power source and of a current and a voltage from the high voltage power source, the power meter configured to provide an indirect measure of output power of the electron beam radiation source.

23. The system of claim 22, further comprising current transformers operatively connected for monitoring the current from the power source and the current from the power input.

24. The system of claim 22, wherein the power meter further comprises an input/output device for communicating with a network, and further comprising a control system for operating the sterilizer.

25. The system of claim 23, wherein the control system comprises a computer and a computer program for operating the sterilizer.

* * * * *